United States Patent
Jeong et al.

(10) Patent No.: US 10,092,651 B2
(45) Date of Patent: Oct. 9, 2018

(54) HIGH-CONTENT FAST DISSOLVING FILM WITH MASKING OF BITTER TASTE COMPRISING SILDENAFIL AS ACTIVE INGREDIENT

(71) Applicant: SEOUL PHARMA CO., LTD., Gyeonggi-do (KR)

(72) Inventors: Hyun Jun Jeong, Gyeonggi-do (KR); Ik Hyeon Chang, Gwangju (KR); Dal Geun Kim, Gangwon-do (KR); Jin Hoo Lee, Seoul (KR); Jin Hee Um, Gyeonggi-do (KR); Hyun Soo Kim, Gyeonggi-do (KR); Kyung Tae Jung, Seoul (KR); Kyu Jeong Yeon, Seoul (KR); Jin Gyu Park, Gyeonggi-do (KR)

(73) Assignee: SEOUL PHARMA CO., LTD., Gyeonggi-do (KR)

( * ) Notice: Subject to any disclaimer, the term of this patent is extended or adjusted under 35 U.S.C. 154(b) by 0 days.

(21) Appl. No.: 14/379,989

(22) PCT Filed: Feb. 28, 2013

(86) PCT No.: PCT/KR2013/001679
§ 371 (c)(1),
(2) Date: Aug. 20, 2014

(87) PCT Pub. No.: WO2013/129889
PCT Pub. Date: Sep. 6, 2013

(65) Prior Publication Data
US 2015/0025084 A1    Jan. 22, 2015

(30) Foreign Application Priority Data

Feb. 28, 2012 (KR) .................. 10-2012-0020316
Oct. 22, 2012 (KR) .................. 10-2012-0117233

(51) Int. Cl.
| | | |
|---|---|---|
| A61K 47/02 | (2006.01) | |
| A61K 31/519 | (2006.01) | |
| A61K 47/10 | (2017.01) | |
| A61K 47/26 | (2006.01) | |
| A61K 47/36 | (2006.01) | |
| A61K 9/00 | (2006.01) | |
| A61K 9/70 | (2006.01) | |

(52) U.S. Cl.
CPC ............... *A61K 47/02* (2013.01); *A61K 9/00* (2013.01); *A61K 9/0056* (2013.01); *A61K 9/70* (2013.01); *A61K 9/7007* (2013.01); *A61K 31/519* (2013.01); *A61K 47/10* (2013.01); *A61K 47/26* (2013.01); *A61K 47/36* (2013.01)

(58) Field of Classification Search
CPC ........ A61K 47/02; A61K 31/519; A61K 9/70; A61K 47/10; A61K 47/26; A61K 47/36; A61K 9/00
See application file for complete search history.

(56) References Cited

U.S. PATENT DOCUMENTS

| | | | |
|---|---|---|---|
| 5,633,006 A * | 5/1997 | Catania et al. | ............... 424/441 |
| 6,552,024 B1 | 4/2003 | Chen et al. | ............. 514/252.16 |
| 7,615,235 B2 | 11/2009 | Rademacher et al. | ........ 424/441 |
| 2006/0100214 A1* | 5/2006 | Tian | ..................... A61K 9/1617 |
| | | | 514/252.16 |
| 2007/0092553 A1 | 4/2007 | Tengler et al. | ............... 424/440 |
| 2007/0292515 A1* | 12/2007 | Schobel | ................ A61K 9/006 |
| | | | 424/487 |
| 2008/0220029 A1 | 9/2008 | Ng et al. | ........................ 424/401 |
| 2008/0233174 A1 | 9/2008 | Myers et al. | ................. 424/435 |
| 2009/0047330 A1* | 2/2009 | Bangalore | ..................... 424/443 |
| 2009/0311327 A1* | 12/2009 | Roberts | ................ A61K 9/2009 |
| | | | 424/489 |
| 2010/0173940 A1 | 9/2010 | Leichs et al. | .................. 514/319 |
| 2010/0297232 A1 | 11/2010 | Myers et al. | ................. 424/484 |

FOREIGN PATENT DOCUMENTS

| | | |
|---|---|---|
| KR | 10-0262926 | 5/2000 |
| KR | 10-0353014 | 9/2002 |
| KR | 10-0354310 | 9/2002 |
| KR | 10-0357411 | 10/2002 |
| KR | 10-0430355 | 4/2004 |
| KR | 10-0627199 | 9/2006 |
| KR | 10-2007-0100023 | 10/2007 |

(Continued)

OTHER PUBLICATIONS

International Search Report (ISR) in PCT/KR2013/001679, dated Jul. 31, 2013.

*Primary Examiner* — Doan T Phan
(74) *Attorney, Agent, or Firm* — Harness, Dickey & Pierce, P.L.C.

(57) ABSTRACT

Provided is a fast dissolving film composition comprising a medically active component as an active ingredient, in which the bitter taste of the active ingredient is masked and the fast dissolving film composition has a high content of 50% or higher. More particularly, provided is a pharmaceutical composition which comprises sildenafil or pharmaceutically acceptable salts thereof as an active ingredient, and which comprises a combination of a specific bitter taste masking agent to achieve masking of a bitter taste. Further, provided is a fast dissolving film composition which comprises a combination of a specific plasticizer to mask a bitter taste, and in which the physical properties of the high-content film are excellent.

2 Claims, No Drawings

(56) References Cited

FOREIGN PATENT DOCUMENTS

| | | |
|---|---|---|
| KR | 10-2009-0080037 | 7/2009 |
| KR | 10-2010-0138768 | 12/2010 |
| KR | 10-1074271 | 10/2011 |
| KR | 10-2012-0101301 | 9/2012 |
| KR | 10-1188594 | 9/2012 |
| WO | WO 2001/070194 | 9/2001 |
| WO | WO200205820 A1 * | 1/2002 |
| WO | WO 2003/070227 | 8/2003 |

* cited by examiner

HIGH-CONTENT FAST DISSOLVING FILM WITH MASKING OF BITTER TASTE COMPRISING SILDENAFIL AS ACTIVE INGREDIENT

CROSS-REFERENCE TO RELATED APPLICATIONS

This application is a national phase application of PCT Application No. PCT/KR2013/001679, filed on Feb. 28, 2013, which claims the benefit and priority to Korean Patent Application No. 10-2012-0117233, filed Oct. 22, 2012 and Korean Patent Application No. 10-2012-0020316, filed Feb. 28, 2012. The entire disclosures of the applications identified in this paragraph are incorporated herein by references.

FIELD

The present invention relates to a fast dissolving film including a high dose of sildenafil or a pharmaceutically acceptable salt thereof. More specifically, the present invention relates to a fast dissolving film containing at least 100 mg of sildenafil or a pharmaceutically acceptable salt thereof per sheet or 50% by weight of sildenafil or a pharmaceutically acceptable salt with respect to the total weight of the film, which previously has been considered impossible, due to the use of a predetermined amount of a specific plasticizer.

The present invention also relates to a fast dissolving film containing sildenafil or a pharmaceutically acceptable salt thereof as an active ingredient whose bitter taste is masked. More specifically, the present invention relates to a fast dissolving film containing sildenafil or a pharmaceutically acceptable salt thereof as an active ingredient and a specific taste masking agent.

Finally, the present invention relates to an orally fast dissolving film containing a high dose of sildenafil or a pharmaceutically acceptable salt thereof as an active ingredient and a specific taste masking agent or a combination of specific taste masking agents to mask the bitter taste of the active ingredient without adversely affecting the film formation.

BACKGROUND

Erectile dysfunction is defined as an inability to induce and sustain penile erection adequate for sexual intercourse, or refers to a condition of the inability to enjoy satisfactory sexual life due to ejaculation disorders such as premature ejaculation and delayed ejaculation or to reach orgasm. It is known that 3 to 5% of the men between 18 and 75 years of age in the United States suffer from chronic erectile dysfunction and most of them are 55 years and older.

Drugs capable of inhibiting subtype 5 of cGMP phosphodiesterase (PDEv inhibitors) can be used for erectile dysfunction treatment. PDEv inhibitors inhibit degradation of cGMP to increase the concentration of cGMP in tissues. Increased cGMP concentration in tissues leads to relaxation of penile smooth muscle to increase the amount of blood flowing into the penile spongy tissues, thus contributing to the treatment of erectile dysfunction.

Examples of PDEv inhibitors heretofore known include vardenafil ([3-(1,4-dihydro-5-methyl-4-oxo-7-propylimidazo[5,1-f][1,2,4]triazin-2-yl)-4-ethoxyphenyl]sulfonyl]-4-ethyl, $C_{23}H_{32}N_6O_4S$, CAS No. 224785-90-4), sildenafil (1-[[3-(6,7-dihydro-1-methyl-7-oxo-3-propyl-1H-pyrazolo[4,3-d]pyrimidin-5-yl)-4-ethoxyphenyl]sulfonyl]-4-methyl-piperazine, $C_{22}H_{30}N_6O_4S$, CAS No. 171599-83-0), tadalafil (pyrazino[1',2'1,6]pyrido[3,4-b]indole-1,4-dione, 6-(1,3-benzodioxol-5-yl)-2,3,6,7,12,12a-hexahydro-2-methyl-, (6R,12aR)—, $C_{22}H_{19}N_3O_4$, CAS No. 171596-29-5), and udenafil, $C_{25}H_{36}N_6O_4S$, CAS No. 268203-93-6). vardenafil, sildenafil, tadalafil, and udenafil, together with medicinal uses thereof, are disclosed in Korean Patent Nos. 0430355, 0262926, 0357411, and 0353014, respectively. For rapid absorption and good bioavailability, such PDEv inhibitors and water soluble salts are prepared into tablets, which are currently sold as oral therapeutic agents for erectile dysfunction.

Of these PDEv inhibitors, sildenafil is a drug for the treatment of erectile dysfunction and the treatment and prophylaxis of angina and pulmonary hypertension. Sildenafil was originally developed and clinically tested as a therapeutic agent for angina. During clinical testing, sildenafil was found to be particularly effective in penile erection. Based on this finding, sildenafil was developed as a therapeutic agent for erectile dysfunction. Since approval by the United States FDA in March, 1998, sildenafil citrate has been commercialized and most widely used as a pharmaceutical drug associated with erectile dysfunction treatment. Sildenafil citrate has been sold under the trade name Viagra® tablet since October, 1999.

In many cases, sildenafil is irregularly administered just before sexual activity. In some cases, sildenafil needs to be administered urgently in unexpected situations on account of its characteristics, and it is thus preferred to carry sildenafil in a convenient manner. In view of the foregoing, attempts have been made to develop sildenafil into formulations that can be easily taken without water rather than into general tablets or capsules.

For example, Korean Patent Publication No. 2007-0100023 discloses an orally fast dissolving formulation of PDE-5 inhibitors which contains a PDEv inhibitor such as sildenafil as an active ingredient. This formulation is an orally disintegrating tablet (ODT) using a solid dispersion in which sildenafil is included in a cyclodextrin.

Korean Patent No. 627199 discloses an orally fast dissolving film (ODF) including sildenafil citrate as an active ingredient. This formulation uses a hydrocolloid as a film-forming polymer. A starch graft copolymer is used to enhance the adhesion of the film formulation to the mucosa.

On the other hand, fast dissolving films including sildenafil are readily disintegrated or dissolved in the oral cavity and can be taken even without water, thus being very useful for the elderly who suffer from difficulty in swallowing tablets or capsules, disabled children, patients lying in bed, and busy modern people. Liquid preparations can be presented as substitutes for tablets or capsules to the elderly and children. However, liquid preparations have the disadvantages of poor stability and inaccurate dose.

Particularly, absorption of a drug through the oral mucous membrane can avoid the liver first-pass effect. Therefore, fast dissolving films are novel useful formulations that can also be applied to drugs highly susceptible to hepatic metabolism among drugs absorbed from the digestive tract.

Typical film preparations are disintegrated within 1 minute and are generally processed to have a thickness of 50 to 150 µm and a size of 22 mm (width)×32 mm (length), which corresponds to an area of 7 cm². Some film preparations may be slightly elongated in width and length. However, there has been no report on preparations having an area of 10 cm² taking into consideration the convenience of administration to patients. Due to the limited thickness and size, currently commercially available fast dissolving film products have a weight of about 50 mg to about 150 mg per sheet.

Despite the convenience of such film preparations, the limited weight per sheet hinders the application to high-dose preparations. Gas-X Thin Strips® from Novartis is known to be the only commercially available fast dissolving film preparation that includes 50% or more of simethicone as an active ingredient. Specifically, this film preparation has a weight of 110 mg per sheet and contains 62.5 mg of the active ingredient. That is, the active ingredient accounts for 57% of the film sheet. It is generally known that an appropriate content of an active ingredient per sheet is about 30% or less. If the content of an active ingredient in a film is 30% or more, the film has poor physical properties, resulting in an increase in brittleness, and is breakable during production and distribution. These disadvantages make it difficult to commercialize the film. Gas-X Thin Strip is the only commercially available fast dissolving film preparation that includes 50% or more of the active ingredient and has relatively good resistance to brittleness.

Sildenafil citrate-containing preparations are currently sold by Pfizer under the brand name of Viagra® and are commercially available in three doses of 25 mg, 50 mg and 100 mg. In the 100 mg preparation, 100 mg of sildenafil corresponds to 140.45 mg of sildenafil citrate, which is greater than that in the currently commercially available preparation Gas-X. Accordingly, a preparation containing 50% or more of sildenafil as an active ingredient should be designed such that 100 mg of sildenafil is processed into a film preparation. For example, a film containing 50% by weight of sildenafil citrate as an active ingredient may have a weight of about 281 mg, which corresponds to a thickness of 280 μm. In this case, the physical properties and brittleness resistance of the film are considerably deteriorated due to the excessive film thickness, making it difficult to produce the film.

Coating, ion exchange resin adsorption or the use of a masking aid is further required to mask the extremely bitter taste of sildenafil citrate, which increases the thickness of the film and deteriorates the physical properties and brittleness of the film.

In an attempt to overcome such disadvantages, U.S. Patent Publication No. 2008/0220029 discloses a fast dissolving film containing an active ingredient including at least 40% of the film weight. The Examples section of this patent publication describes taste masked fast dissolving films containing previously coated active ingredients such as ibuprofen.

U.S. Patent Publication No. 2008/0233174 discloses a fast dissolving film containing at least 30% by weight of an active ingredient, based on the weight of the film. The Examples section of this patent publication describes the use of encapsulated acetaminophen. The high-dose fast dissolving film is produced after previous masking of the active ingredient through coating or encapsulation with two kinds of polymers having different glass transition temperatures. U.S. Pat. No. 6,552,024 describes a fast dissolving film containing sildenafil citrate. However, this patent fails to describe how to mask the bitter taste of sildenafil citrate as an active ingredient. An active ingredient of a fast dissolving film preparation is disintegrated or dissolved in the oral cavity on account of the characteristics of the preparation. At this time, a bitter or unpleasant taste of the active ingredient should be masked for industrial applicability of the preparation. In connection with the taste masking of a sildenafil preparation, U.S. Patent Publication No. 2009/0047330 discloses an orally fast dissolving film composition of a PDE-5 inhibitor containing a PDEv inhibitor such as sildenafil as an active ingredient. The Examples section of this patent publication describes masking of sildenafil with cyclodextrins.

Other approaches to mask inherent bitter tastes of drugs are disclosed in the literature. For example, PCT International Publication No. WO 2001/70194 discloses the production of a fast dissolving orally consumable film by adsorbing an active ingredient to an ion exchange resin as a taste masking agent. For masking the taste of the active ingredient, the resin should be used in an amount of 1 to 3 times the amount of the active ingredient, making it difficult for the fast dissolving film to include a high dose 50%) of the active ingredient. Further, PCT International Publication No. WO 2003/070227 describes the use of a carbon dioxide-forming substance such as sodium bicarbonate for taste masking. Disadvantageously, sodium bicarbonate is limited in masking a strong bitter taste of a drug.

Korean Patent Registration No. 1074271 describes a fast dissolving film using a stevioside-based sweetener and a high-potency sweetener to effectively mask an unpleasant taste. This is an attempt to suppress a bitter taste of an active ingredient using a combination of general sweetening agents but is limited in the application to a very bitter drug such as sildenafil citrate. In the Examples section of this patent document, an active ingredient is used in an amount of 0.1 to 30% by weight with respect to the weight of the film, but the use of 40% by weight or more of an active ingredient with respect to the total weight of the formulation cannot be found. U.S. Patent Publication No. 2007/0292515 discloses an approach to mask the bitter taste of ketoprofen. According to this approach, the pH of the ketoprofen is increased using an alkalizing agent such as sodium hydroxide, and the ketoprofen is then loaded in a film formulation. Korean Patent No. 354310 discloses the use of a basic buffer solution or a pH-adjusting agent to minimize the bitter taste of azithromycin. Korean Patent No. 10-1188594 discloses the use of sodium hydroxide, sodium bicarbonate or a mixture thereof to mask the bitter taste of sildenafil citrate. Korean Patent Publication No. 10-2012-0101301 discloses a technique associated with the use of a sildenafil free base. The Examples section of this patent publication describes the use of 50% or less of the active ingredient.

Based on the above, to the best of our knowledge, no report has appeared on an orally fast disintegrating film formulation with markedly improved brittleness resistance including at least 50% of sildenafil or a pharmaceutically acceptable salt thereof as an active ingredient whose bitter taste is masked. Bitter taste masking of an active ingredient inevitably leads to poor physical properties and brittleness resistance of a film. Meanwhile, good physical properties of a film indicate the presence of a small dose of an active ingredient in the film. Therefore, it is difficult to produce a fast dissolving film formulation containing Viagra 100 mg currently available in the market.

SUMMARY

Thus, it is an object of the present invention to provide fast dissolving films including a high dose of sildenafil or a pharmaceutically acceptable salt thereof. The specific reason why a high dose of an active ingredient is not loaded in film formulations of the prior art is that the presence of 50% by weight of the active ingredient with respect to the total weight of the film causes a serious problem in the brittleness of the film. Based on this reason, it is an object of the present invention to provide fast dissolving films that are free from the problem of brittleness even when a high dose of an active ingredient is loaded. Further, the present inventors have found that even when a high dose of sildenafil as an active ingredient is loaded and the problem of brittleness is solved, the medication compliance of a patient upon administration is greatly deteriorated by ineffective masking of the bitter taste of the active ingredient. Considering this finding, it is another object of the present invention to provide a taste masking agent specially designed to produce a desired formulation.

Particularly, it is an object of the present invention to provide a fast dissolving film including sildenafil whose bitter taste is masked by a specific taste masking agent and/or a combination of specific taste masking agents. Furthermore, it is an object of the present invention to provide a pharmaceutical composition that has good ability to form an orally fast disintegrating and dissolving film containing sildenafil or a pharmaceutically acceptable salt thereof as an active ingredient whose bitter taste is masked by a combination of specific taste masking agents.

It is a final object of the present invention to provide a fast dissolving film including a high dose of sildenafil or a pharmaceutically acceptable salt thereof whose bitter taste is completely masked by a specific taste masking agent and/or a combination of specific taste masking agents. Further, the present invention is of technical significance in providing a fast dissolving film in which a high dose of an active ingredient is loaded and the bitter taste of the active ingredient is effectively masked without causing any problem in film-forming ability.

DETAILED DESCRIPTION

The present invention discloses a fast dissolving film including sildenafil or a pharmaceutically acceptable salt thereof, a water soluble hydrocolloid, and a plasticizer wherein the sildenafil or pharmaceutically acceptable salt thereof is present in an amount of at least 100 mg or at least 50% by weight with respect to the total weight of the film.

The plasticizer is selected from the group consisting of glycerin fatty acid esters, sucrose fatty acid esters, lecithin, enzyme modified lecithin, polysorbates, sorbitan fatty acid esters, sorbitol, maltitol, xylitol, glycerin, polyethylene glycol, propylene glycol, hydrogenated starch syrup, starch syrup, glycerin, triacetin, glycerol oleate, and medium chain fatty acids.

The plasticizer includes glycerin or sorbitol.

The water soluble hydrocolloid is selected from the group consisting of pullulan, gelatin, pectin, low viscosity pectin, hydroxypropylmethyl cellulose, low viscosity hydroxypropylmethyl cellulose, hydroxyethyl cellulose, hydroxypropyl cellulose, carboxymethyl cellulose, polyvinyl alcohol, polyacrylic acid, methyl methacrylate copolymer, carboxyvinyl polymer, polyethylene glycol, alginic acid, low viscosity alginic acid, sodium alginate, carrageenan, modified starch, casein, whey protein extract, soy protein extract, zein, levan, elsinan, gluten, *acacia* gum, gum arabic, guar gum, locust bean gum, xanthan gum, gellan gum, and agar.

Preferably, the hydrocolloid is selected from the group consisting of pullulan, xanthan gum, locust bean gum, polyvinyl alcohol, pectin, low viscosity pectin, low viscosity alginic acid, and hydroxypropylmethyl cellulose.

The present invention also discloses a fast dissolving film including sildenafil or a pharmaceutically acceptable salt thereof and a water soluble hydrocolloid wherein the fast dissolving film includes a taste masking agent selected from the group consisting of sodium hydroxide, calcium phosphate, potassium hydroxide, calcium hydroxide, magnesium oxide, potassium dihydrogen phosphate, sodium dihydrogen phosphate, calcium chloride, and potassium chloride.

The taste masking agent is sodium hydroxide and/or magnesium oxide.

The taste masking agent is a mixture of magnesium oxide and sodium hydroxide in a ratio of 1:4 to 4:1.

The present invention also discloses a method for producing a fast dissolving film, the method including: (a) homogenizing sildenafil citrate, a film-forming agent, a plasticizer, a taste masking agent, and a pharmaceutically acceptable additive with stirring to provide a composition for an oral film formulation;

(b) feeding the composition into a molding machine and shaping the composition into a film; and (c) slitting and cutting the film, and filling the film pieces in a container or aluminum packaging paper to produce an oral film formulation, wherein the taste masking agent is selected from the group consisting of magnesium oxide and sodium hydroxide, and the film formulation includes at least 100 mg of sildenafil citrate or at least 50% by weight of sildenafil citrate with respect to the total weight of the film.

The plasticizer includes glycerin or sorbitol.

In the method of the present invention, at least one high-potency sweetener selected from the group consisting of aspartame, thaumatin or thaumatin mixture, and sucralose is used as a sweetening agent.

In the method of the present invention, a mixture of aspartame, sucralose, and thaumatin dextrin in a ratio of 1:1.5:2 is used as the high-potency sweetening agent.

The present invention also discloses a method for producing a fast dissolving film, the method including:

homogenizing a sildenafil base, a film-forming agent, a plasticizer, a taste masking agent, and a pharmaceutically acceptable additive with stirring to provide a composition for producing an oral film formulation;

feeding the composition into a molding machine and shaping the composition into a film; and slitting and cutting the film, and filling the film pieces in a container or aluminum packaging paper to produce an oral film formulation, wherein the plasticizer includes glycerin, sorbitol and/or polyethylene glycol, and the film formulation includes at least 100 mg of sildenafil or at least 50% by weight of sildenafil with respect to the total weight of the film.

In the method of the present invention, at least one high-potency sweetener selected from the group consisting of aspartame, thaumatin or thaumatin mixture, and sucralose is used as a sweetening agent.

In the method of the present invention, a mixture of aspartame, sucralose, and thaumatin dextrin in a ratio of 1:1.5:2 is used as the high-potency sweetening agent.

Advantageous Effects

The fast dissolving films of the present invention include at least 50% by weight of sildenafil or a pharmaceutically acceptable salt thereof with respect to the total weight of the film or at least 100 mg of sildenafil or a pharmaceutically acceptable salt thereof per sheet. In addition, the fast dissolving films of the present invention are free from the problem of brittleness and can effectively mask the bitter taste of the active ingredient even when the amount of the active ingredient loaded exceeds the limitation encountered in general film formulations.

Best Mode

A general tablet or capsule formulation of a bitter drug stays in the oral cavity for only an extremely short time and is not substantially dissolved in the oral cavity. Accordingly, a patient does not feel inconvenienced by the bitter taste of the drug after having taken the formulation. However, an orally disintegrating formulation (e.g., an orally fast disintegrating tablet (ODT) or an orally fast disintegrating film (ODF) formulation) including a bitter drug is disintegrated and/or dissolved while staying in the oral cavity for at least several seconds to as many as several minutes. Accordingly, a patient cannot help but feel the bitter taste of the drug after having taken the formulation. There is thus a need to develop an appropriate approach to mask the bitter taste. The most common approach to mask bitter tastes is to use various kinds of sweetening agents. In many cases, however, the presence of sweetening agents in formulations does not completely mask bitter tastes to the extent that patients cannot feel the bitter tastes. In view of this situation, many approaches have been proposed to mask bitter tastes. Examples of such approaches include controlling the particle size of active ingredients, using inclusion compounds, coating drugs with insoluble polymers, and using solid dispersions.

However, these approaches create large differences in taste masking effects depending on the physical properties of individual drugs and the forms of final formulations. Consequently, it is to be understood that an approach effective in a certain specific drug and a specific formulation is not always applicable to other active ingredients and formulations.

On the other hand, attempts have been continuously made to process PDEv inhibitors, for example, extremely bitter sildenafil citrate, into orally fast disintegrating formulations such as ODTs or ODFs. Thus, numerous approaches have been employed to mask bitter tastes but are considered insufficient to effectively mask bitter tastes without impairing the inherent characteristics of ODT or ODF formulations.

Particularly, the pharmaceutical compositions of the present invention can be prepared into, for example, oral film formulations. Such oral film preparations can overcome difficulty in and fear of taking in patients such as the elderly or the disabled suffering from dysphagia and can be administered in accurate doses to ensure improved stability and efficacy when compared to liquid preparations. Oral film preparations can be designed such that drugs can be directly delivered to desired sites through the oral mucosal membrane without liver first-pass effect. Therefore, the use of oral film preparations contributes to improvement of bioavailability to obtain more rapid efficacy in a relatively low dose. Oral film formulations can be individually packaged in very thin packaging materials, unlike other formulations. This unit packaging makes oral film formulations simple to carry and store. Furthermore, oral film formulations can be developed to replace tablets, capsules or liquid syrup formulations of currently marketed drugs for children and the elderly, therapeutic agents for cerebral nerve diseases, and therapeutic agents for erectile dysfunction. Drug delivery systems (DDSs) using such oral film formulations can offer the opportunity to increase the going concern value and profit level of pharmaceutical companies.

Despite such advantages, however, several technical difficulties exist in formulating PDEv inhibitors, for example, sildenafil or pharmaceutically acceptable salts thereof, into oral film preparations.

The first problem is associated with the ability to form films and the amount of active ingredients loaded. For example, when it is intended to process currently commercially available Viagra 50 mg and 100 mg tablets including sildenafil citrate as an active ingredient into fast dissolving film formulations, it is necessary to load 100 mg or more of sildenafil (corresponding to 140.45 mg or more of sildenafil citrate) in the film formulations. However, loading of 100 mg or more of the active ingredient in the film formulation is considered very technically difficult. The reason for this difficulty is explained as follows. An increase in the amount of the active ingredient requires an increase in the amount of a film-forming agent used, but the size, thickness and total weight of the formulation are strictly restricted because of the requirement that the film formulation should be quickly disintegrated in the oral cavity. Accordingly, loading of 100 mg or more of the active ingredient within the limited total weight range of the film formulation means that the amount of a film-forming agent or other additives included in the formulation should be reduced. In conclusion, it is difficult to load a large amount of the active ingredient while maintaining good film-forming ability and excellent physical properties. Particularly, according to the present inventors' research, when 100 mg or more of sildenafil citrate is loaded in accordance with a conventional film production method, the problem of brittleness becomes serious, making it impossible to form a commercially available fast dissolving film. That is, when the amount of sildenafil is forcedly increased to 100 mg or above in accordance with a conventional production method, either a film is not formed or it tends to be brittle. When the film is administered to a patient after storage and distribution, its inherent shape cannot be maintained. For these reasons, attempts to commercialize oral films including 100 mg or more of sildenafil citrate have not been successful.

The second problem is that it is difficult to draw an approach to mask the bitter taste of sildenafil citrate without affecting the ability to form a fast dissolving film including a high dose of sildenafil citrate. The present inventors have earnestly conducted repeated research on various conventional approaches to mask bitter tastes of drugs included in oral films. As a result, the present inventors have found that when the conventional approaches are applied to fast dissolving films including high doses of the active ingredients, the bitter tastes of the active ingredients are not effectively masked. The present inventors have also found that when the conventional approaches are employed, either films are not formed or their quality is extremely poor, thus being unsuitable as commercially available products. Specifically, the present inventors have found that when at least 100 mg of sildenafil citrate is included as in the present invention in accordance with a conventional production method and a known approach to mask a bitter taste is applied thereto, the film-forming ability is seriously affected. Since the formulations of the present invention include 50% by weight of the active ingredient with respect the total weight of the film, other ingredients, for example, a film-forming agent, are present in very small amounts compared to those of conventional compositions. Under such circumstances, known approaches to mask bitter tastes are not applicable to the present invention.

Accordingly, the formulations of the present invention including a high dose of sildenafil citrate are required to employ a specially designed approach to mask the bitter taste of the active ingredient.

The third problem is associated with the brittleness of fast dissolving films including high doses of active ingredients. When a high dose of an active ingredient is included as in the present invention in accordance with a conventional production method, either a film is not readily formed or it suffers from serious problems in terms of properties and shape. The presence of a large amount of an active ingredient in a fast dissolving film inevitably leads to a reduction in the amount of a film-forming agent. Due to the use of a reduced amount of the film-forming agent, the film tends to be brittle even when a small impact is applied thereto during storage. For this reason, it is considered practically impossible in the art to manufacture a film formulation containing at least 100 mg of sildenafil citrate into an industrially available product.

Particularly, the above three problems are very difficult to solve simultaneously in that they do not arise independently from each other but are organically related to each other. That is, when a sweetening agent is used in a large amount or a cyclodextrin is used as an approach to enhance the ability to mask a bitter taste, a high dose of an active ingredient cannot be loaded in a fast dissolving film and a problem may arise in the ability to form the film or the problem of brittleness cannot be solved. An increased amount of a film-forming agent may be used to solve the problem of brittleness. In this case, however, there exists a limitation in increasing the amount of an active ingredient. Thus, there is a need for a novel and inventive composition that can mask the bitter taste of an active ingredient and solve the problem of brittleness while maximizing the amount of the active ingredient.

As a result of repeated research, the present inventors have succeeded in drawing new techniques to simultaneously solve the above problems, i.e. techniques to include a high dose of an active ingredient, to effectively mask the bitter taste of the active ingredient while maintaining good film-forming ability, and to solve the problem of brittleness, and finally arrived at the present invention. Specifically, as a result of repeated research, the present inventors have found that when a specific plasticizer is used in a predetermined amount and a combination of sodium hydroxide and magnesium oxide is used as a taste masking agent to produce a fast dissolving film including a high dose of sildenafil or a pharmaceutically acceptable salt thereof as an active ingredient, the problem of brittleness can be solved and the bitter taste of the active ingredient can be effectively masked. The present invention has been achieved based on this finding.

More specifically, the oral film formulation of the present invention may contain a therapeutically effective amount of an active ingredient, an alkalizing agent, a high-potency sweetener, a film-forming agent, and pharmaceutically acceptable additives. The oral film formulation of the present invention is completely disintegrated and/or dissolved in the oral cavity within 100 seconds, preferably 60 seconds, more preferably 30 seconds after taking without water, and is absorbed from the gastrointestinal tract.

More specifically, the oral film formulation of the present invention preferably includes a high dose of sildenafil or a pharmaceutically acceptable salt thereof, i.e. at least 50% by weight of sildenafil or a pharmaceutically acceptable salt thereof with respect to the total weight of the film or at least 100 mg of sildenafil or a pharmaceutically acceptable salt thereof per sheet, a taste masking agent, a plasticizer, a sweetening agent, a film-forming agent, and other additional ingredients. The additional ingredients may be pharmaceutically acceptable additives, such as a thickener, a filler, a sweetening agent, an acidulant, a flavor, a surfactant, a water soluble polymer, a preservative, a colorant, and a cooling agent, which will be described in detail.

Taste Masking Agent

A general tablet or capsule formulation of a bitter drug stays in the oral cavity for only an extremely short time and is not substantially dissolved in the oral cavity. Accordingly, a patient does not feel inconvenienced by the bitter taste of the drug after having taken the formulation. However, an orally disintegrating formulation (e.g., an orally fast disintegrating tablet (ODT) or an orally fast disintegrating film (ODF) formulation) including a bitter drug is disintegrated and/or dissolved while staying in the oral cavity for at least several seconds to as many as several minutes. Accordingly, a patient cannot help but feel the bitter taste of the drug after having taken the formulation. There is thus a need to develop an appropriate approach to mask the bitter taste. The most common approach to mask bitter tastes is to use various kinds of sweetening agents. In many cases, however, the presence of sweetening agents in formulations does not completely mask bitter tastes to the extent that patients cannot feel the bitter tastes. In view of this situation, many approaches have been proposed to mask bitter tastes. Examples of such approaches include controlling the particle size of active ingredients, using inclusion compounds, coating drugs with insoluble polymers, and using solid dispersions.

However, these approaches create large differences in taste masking effects depending on the physical properties of individual drugs and the forms of final formulations. Consequently, it is to be understood that an approach effective in a certain specific drug and a specific formulation is not always applicable to other active ingredients and formulations.

On the other hand, attempts have been continuously made to process PDEv inhibitors, for example, extremely bitter sildenafil citrate, into orally fast disintegrating formulations such as ODTs or ODFs. Thus, numerous approaches have been employed to mask bitter tastes but are considered insufficient to effectively mask bitter tastes without impairing the inherent characteristics of ODT or ODF formulations. In the case where the general taste masking approaches explained above are applied to the formulations of the present invention containing a high dose of the active ingredient, excellent taste masking effects are not obtained, the problem of brittleness are caused, or the films are not formed.

Thus, the present invention discloses a new approach to mask a bitter taste. In the present invention, a taste masking agent is used to adjust the pH of a composition for the formation of the oral film to the range of 4.8 to 7 for the purpose of masking the bitter taste of sildenafil citrate. According to the present inventors' research, the bitter taste of the oral film preparation containing sildenafil citrate cannot be effectively masked by a general sweetening agent. Based on this research result, the present inventors have earnestly investigated, and as a result, found that the bitter taste disappears when the pH range of the composition is adjusted to the range defined above using a specific taste masking agent and/or a combination of specific taste masking agents. According to the present inventors' further research, it was found that the bitter taste is masked to some extent by the limited pH range but, in some cases, sufficient taste masking effects may not be obtained depending on the kinds of the specific substances used and, above all, problems arise in film-forming ability and brittleness.

In the present invention, an appropriate pH-adjusting agent may be used to increase the pH of the composition, and examples thereof include sodium carbonate, sodium bicarbonate, potassium bicarbonate, sodium phosphate, potassium phosphate, calcium carbonate, magnesium carbonate, sodium hydroxide, magnesium hydroxide, potassium hydroxide, and aluminum hydroxide. The amount of the taste masking agent used may be suitably determined so long as the pH of the composition is adjustable to the range defined above. The taste masking agent is preferably used in an amount of 1.0 to 10.0% by weight. This is the first feature of the present invention.

Another important feature of the present invention lies in that a specific taste masking agent and/or a combination of specific taste masking agents can provide an optimum range where the film formation is not adversely affected, particularly the problem of brittleness is not caused. As a result of research, the present inventors have unexpectedly found that although a taste masking agent can be used to adjust the pH range and a combination of sweetening agents can be used to accomplish bitter taste masking effects, the film formation is not satisfactory and the problem of brittleness arises. That is, even when the pH range is adjusted to the range defined above, it is difficult to practically produce a fast dissolving film formulation including a high dose of sildenafil citrate.

The present inventors have endeavored to solve such problems and found that when a combination of magnesium oxide and sodium hydroxide as a taste masking agent is used to adjust the pH to the range of 4.8 to 7, good film-forming ability is achieved and the problem of brittleness is avoided. Magnesium oxide and sodium hydroxide are preferably used in a ratio of 1:4 to 4:1, and the sum of magnesium oxide and sodium hydroxide is preferably adjusted to 1 to 10%, based on the total weight of the formulation.

Sweetening Agent

The pharmaceutical composition of the present invention may include a sweetening agent. The sweetening agent may be at least one high-potency sweetener selected from the group consisting of sugar, glucose, maltose, oligosaccharides, galactose, starch syrup, sorbitol, maltitol, xylitol, erythritol, hydrogenated starch syrup, mannitol, trehalose, aspartame, acesulfame salts, sucralose, saccharin salts, neotame, thaumatin, thaumatin mixture, cyclamate salts, Luo han guo extract, licorice extract, stevioside, enzyme modified stevioside, neohesperidine, and monellin. More preferably, the sweetening agent is at least one high-potency sweetener selected from the group consisting of aspartame, thaumatin mixture, sucralose, neotame, and acesulfame.

In the case of a drug having a strong unpleasant taste, a patient feels the bitter and unpleasant taste even after having taken the drug. The bitter and unpleasant taste of the drug can be masked by a combination of 1.0 to 10.0% by weight of aspartame with respect to the total weight of the formulation and one or more other sweeteners. Particularly, the use of a combination of aspartame and Talin MD90 can effectively mask the bitter taste, achieve improved film-forming ability, and give a comfortable feeling upon taking.

Film-Forming Agent

The oral film formulation of the present invention includes a water soluble polymer as a film-forming agent. The water soluble polymer may be selected from the group consisting of pullulan, gelatin, pectin, low viscosity pectin, hydroxypropylmethyl cellulose, low viscosity hydroxypropylmethyl cellulose, hydroxyethyl cellulose, hydroxypropyl cellulose, carboxymethyl cellulose, polyvinyl alcohol, polyacrylic acid, methyl methacrylate copolymer, carboxyvinyl polymer, polyethylene glycol, alginic acid, low viscosity alginic acid, sodium alginate, carrageenan, modified starch, casein, whey protein extract, soy protein extract, zein, levan, elsinan, gluten, *acacia* gum, gum arabic, guar gum, locust bean gum, xanthan gum, gellan gum, agar, and mixtures thereof. Preferably, the water soluble polymer is selected from the group consisting of pullulan, gelatin, pectin, low viscosity pectin, low viscosity alginic acid, hydroxypropylmethyl cellulose, modified starch, and mixtures thereof.

The oral film formulation may contain 55 to 70% by weight of the water soluble polymer, based on the total weight of the formulation.

Active Ingredient

The pharmaceutically active ingredient used in the oral film formulation of the present invention may be any pharmacologically active ingredient that can be administered orally.

Examples of pharmaceutically active ingredients suitable for use in the oral film formulation include: therapeutic agents for diabetes mellitus, such as glimepiride and pioglitazone; therapeutic agents for insomnia, such as zolpidem and eszopiclone; therapeutic agents for genitourinary diseases, such as tolterodine and trospium; therapeutic agents for obesity, such as sibutramine; enzymes, such as streptokinase; therapeutic agents for gastric ulcer, such as omeprazole; antitussives and apophlegmatics, such as theophylline and clenbuterol; therapeutic agents for skin diseases, such as finasteride; antiemitics, such as ondansetron; antidepressants, such as fluoxetine; antihistamines, such as fexofenadine hydrochloride; antipyretics, analgesics and antiphlogistics, such as aspirin, ibuprofen, ketoprofen, and meloxicam; hormones, such as testosterone; therapeutic agents for circulatory diseases, such as felodipine, atorvastatin, amlodipine camsylate, doxazosin, simvastatin, and lercanidipine; therapeutic agents for digestive system diseases, such as famotidine, ranitidine, and lansoprazole; therapeutic agents for cardiovascular diseases, such as amlodipine and nitroglycerin; therapeutic agents for psychoneurotic disorders, such as paroxetine; therapeutic agents for erectile dysfunction, such as sildenafil, tadalafil, and vardenafil; therapeutic agents for Alzheimer's disease, such as donepezil; therapeutic agents for osteoporosis; therapeutic agents for arthritis; therapeutic agents for epilepsy; muscle relaxants; cerebral function enhancers; therapeutic agents for schizophrenia; immunosuppressants; antibiotics, such as ampicillin and amoxicillin; anticancer agents; anticancer supplements; vaccines; oral cleansers; antianemics; therapeutic agents for constipation; therapeutic agents for allergic diseases; anticoagulants; oral vaccines; melatonin; vitamins; nutritional supplements; *lactobacillus* preparations; multi-symptom cold medicines; and health functional foods.

The pharmaceutically active ingredient may be selected from the group consisting of triclosan, cetylpyridium chloride, domiphen bromide, quaternary ammonium salts, zinc compounds, sanguinarine, fluorides, alexidine, octonidine, EDTA, aspirin, acetaminophen, ibuprofen, ketoprofen, diflunisal, fenoprofen calcium, naproxen, tolmetin sodium, indomethacin, benzonatate, caramiphen, edisylate, menthol, dextromethorphan hydrobromide, chlophedianol hydrochloride, diphenhydramine, pseudoephedrine, phenylephrine, phenylpropanolamine, pseudoephedrine sulfate, brompheniramine maleate, chlorpheniramine maleate, carbinoxamine maleate, clemastine fumarate, dexchlorpheniramine maleate, diphenhydramine hydrochloride, diphenhydramine citrate, diphenylpyraline hydrochloride, doxylamine succinate, promethazine hydrochloride, pyrilamine maleate, tripelennamine citrate, triprolidine hydrochloride, acrivastine, loratadine, brompheniramine, dexbrompheniramine, guaifenesin, ipecac, calcium iodide, terpine hydrate, loperamide, famotidine, ranitidine, omeprazole, lansoprazole, aliphatic alcohols, nicotine, caffeine, strychnine, picrotoxin, pentylenetetrazol, phenylhydantoin, phenobarbital, primidone, carbamazepine, ethosuximide, methosuximide, phensuximide, trimethadione, diazepam, benzodiazepine, phenacemide, pheneturide, acetazolamide, sulthiame, bromides, levodopa, amantadine, morphine, heroin, hydromorphone, metopon, oxymorphone, levorphanol, codeine, hydrocodone, xycodone, nalorphine, naloxone, naltrexone, salicylate, phenylbutazone, indomethacin, phenacetin, chlorpromazine, methotrimeprazine, haloperidol, clozapine, reserpine, imipramine, tranylcypromine, phenelzine, lithium, apomorphine, sildenafil, tadalafil, vardenafil, ondansetron, donepezil, zolpidem tartrate, granisetron, montelukast, pholcodine, butylscopolamine, fentanyl citrate, oxycodone hydrochloride, buprenorphine hydrochloride, escitalopram oxalate, rivastigmine tartrate, esomeprazole magnesium, aripiprazole, zolmitriptan, rizatriptan benzoate, telmisartan, risperidone, benzocaine, cetirizine hydrochloride, bambuterol hydrochloride, galantamine hydrobromide, lercanidipine hydrochloride, paroxetine hydrochloride, meloxicam, tolterodine tartrate, doxazosin mesylate, pharmaceutically acceptable salts thereof, and mixtures thereof. The active ingredient may be present in an amount up to 75% by weight, based on the total weight of the oral film formulation.

Filler

The oral film formulation may include a filler. The filler serves to increase the density of the film while maintaining the shape of the film. In addition, the filler can reduce the adhesion between films, prevent stickiness of the film, and control the disintegration rate of the film and the dissolution rate of the drug in the oral cavity. The filler may be added in an amount of 0.5 to 10% by weight, based on the total weight of the oral film formulation.

In one embodiment, the filler may be selected from the group consisting of microcrystalline cellulose, cellulose polymers, magnesium carbonate, calcium carbonate, limestone powder, silicate, clay, talc, titanium dioxide, calcium phosphate, and mixtures thereof.

Plasticizer

The oral film formulation of the present invention may include a plasticizer. The plasticizer can be used to control flexibility and brittleness of the film. The present invention features in that the film includes 50% by weight or more of sildenafil citrate with respect to the total weight of the film or at least 100 mg of sildenafil citrate. On the other hand, the problem of brittleness may arise in a formulation including a high dose of sildenafil citrate produced in accordance with a conventional method, making it impossible to practically use the formulation as a commercially available product.

On the other hand, sildenafil citrate preparations are currently sold under the trade name of Viagra® and commercially available in three doses of 25 mg, 50 mg and 100 mg. The 100 mg preparation contains about 140.45 mg of sildenafil citrate. When this preparation is processed into a fast dissolving film preparation including 50% of the active ingredient with respect to the total weight of the film, the weight of the fast dissolving film preparation is increased to 280 mg. However, a preparation weighing 250 mg or more is too large in size to be administered to the oral cavity at one time. If the preparation is limited to a size of 27 mm (width) and 32 mm (length), which is suitable for administration to the oral cavity at one time, the preparation is formed thick, inevitably losing its physical properties and marketability. In contrast, the film formulation of the present invention is limited a width of 27 mm, a length of 32 mm, and a weight of about 220 mg. Despite the limited dimensions and weight, the film formulation of the present invention includes 100 mg of sildenafil.

The fast dissolving film includes a high dose (60 to 70%) of sildenafil citrate per sheet. If this film is produced in accordance with a conventional method, the flexibility and strength of the film are considerably deteriorated. Particularly, the film has poor brittleness resistance. As a result, when the film is subjected to a bending test at 55% RH and 22° C. after unsealing from aluminum packaging foil, it is broken at the initial stage of testing.

The present inventors have earnestly studied to improve the brittleness resistance of a fast dissolving film preparation including a high dose of an active ingredient, and as a result, have found that the use of 1 to 10% of glycerin, 0.1 to 10% of sorbitol and/or a combination thereof enables the production of a fast dissolving film with markedly improved brittleness resistance. That is, when the plasticizer is used, the problem of brittleness is not caused despite the use of a small amount of the film-forming agent. The present inventors have also found the fact that when the plasticizer is combined with a combination of sodium hydroxide and magnesium oxide as the taste masking agent, which is first proposed in the present invention, the bitter taste of the active ingredient is completely removed.

The plasticizer may be selected from the group consisting of glycerin fatty acid esters, sucrose fatty acid esters, lecithin, enzyme modified lecithin, polysorbates, sorbitan fatty acid esters, sorbitol, maltitol, xylitol, glycerin, polyethylene glycol, propylene glycol, hydrogenated starch syrup, starch syrup, glycerin, triacetin, glycerol oleate, medium chain fatty acids, and mixtures thereof. As explained above, glycerin or sorbitol is most preferred.

Acidulant

The oral film formulation of the present invention may further include an acidulant. The acidulant, together with the sweetening agent, is used for taste control and functions to stimulate salivary secretion so as to easily dissolve the edible film. The acidulant may be added in an amount of 0.5 to 10% by weight, based on the oral fast film formulation composition.

In one exemplary embodiment, the acidulant may be selected from the group consisting of citric acid, malic acid, fumaric acid, tartaric acid, ascorbic acid, succinic acid, adipic acid, lactic acid, and mixtures thereof.

Flavor

The oral film formulation of the present invention may include a flavor. The kind of the flavor added is appropriately selected taking into consideration the fact that the oral film formulation of the present invention is dissolved and absorbed in the oral cavity. The flavor may a natural flavor, an artificial flavor or a mixture thereof.

Examples of suitable natural flavors include extracts from leaves, flowers and fruits of plants, and oils from plants. The plant oils include spearmint oil, cinnamon oil, peppermint oil, lemon oil, clove oil, bay oil, thyme oil, cedar leaf oil, nutmeg oil, sage oil, and almond oil. Examples of suitable artificial flavors include synthetic fruit flavors, such as synthetic lemon, orange, grape, lime, and strawberry flavors, and other synthetic flavors, such as synthetic vanilla, chocolate, coffee, cocoa, pine leaf, *ginseng*, red *ginseng*, and citrus flavors.

The amount of the flavor used may vary depending on various factors, such as the type, kind and desired intensity of the flavor, and is typically from 0.1 to 10.0% by weight, based on the oral film formulation. When the flavor is of oil type, an emulsifier may be used for miscibility with water soluble substances. The amount of the emulsifier used may vary depending on the kind and amount of the flavor and may be from 0.5 to 10% by weight, based on the total weight of the oral film formulation.

Colorant

The oral film formulation of the present invention may include a suitable colorant for the product. The content of the colorant may be appropriately determined according to the intended purpose and may be from 0.1 to 1.0% by weight, based on the total weight of the oral film formulation. The colorant may be a natural or synthetic colorant.

Cooling Agent

The oral film formulation of the present invention may further include a cooling agent. The cooling agent is not particularly limited and may be, for example, 1-menthol, WS3, WS23 or Questice-L. The content of the cooling agent may be appropriately determined according to the intended purpose and may be typically 10% by weight or less, based on the total weight of the oral film formulation.

Breath Freshener

The oral film formulation of the present invention may further include a breath freshener to alleviate oral malodor.

The breath freshener may be a metal salt. For example, the metal salt may be selected from the group consisting of metal chlorites, copper gluconate, zinc chloride, zinc citrate, zinc gluconate, and mixtures thereof. In a further embodiment, the breath freshener may be selected from the group consisting of triclosan, alexidine, hexetidine, benzalkonium chloride, salicylanilide, domiphen bromide, tetradecylpyridinium chloride, N-tetradecyl-4-ethylpyridinium chloride, octenidine, iodine, sulfonamide, bisbiguanide, phenols, delmopinol, octapinol, chlorhexidine, nisin preparations, nystatin, sanguinarine, cetylpyridinium chloride, red *ginseng* extracts, green tea extracts, seaweed extracts, herb extracts, grapefruit extracts, apple extracts, thyme oil, thymol, antibiotics, geraniol, carvacrol, citral, hinokitiol, ucalyptol, catechol, methyl salicylate, hydrogen peroxide, and mixtures there. The breath freshener may be used either independently or together with one or more of the metal salts.

It would be desirable that the oral film formulation of the present invention is formed into a thin film while maintaining tensile strength and toughness at desired levels.

In one embodiment, the oral film formulation of the present invention has a thickness of 50 µm to 300 µm, preferably 60 µm to 280 µm, most preferably 70 µm to 260 µm. The oral film formulation of the present invention has a size of 1 cm$^2$ to 12 cm$^2$, preferably 2 cm$^2$ to 10 cm$^2$, more preferably 4 cm$^2$ to 8 cm$^2$.

The present invention also provides a method for producing the oral film formulation. In one embodiment, the method includes:

a. mixing an active ingredient, two kinds of high-potency sweeteners, and a water soluble polymer to prepare a composition for the oral film formulation;

b. feeding the composition into a molding machine and shaping the composition into a film at 15 to 150° C., preferably 25 to 120° C., more preferably 40 to 100° C.; and c. aging the film at 30 to 90% relative humidity for 1 to 30 days.

More specifically, the method of the present invention may be carried out, for example, through the following processes.

Composition preparation: An active ingredient, an alkalizing agent, a surfactant, and a plasticizer are homogenized with stirring, and then a sweetening agent, a flavor, a water soluble polymer, and a coloring agent were added thereto. The mixture is homogenized with stirring to prepare a composition for the oral film formulation. The final pH of the composition is adjusted to the range of 4.8 to 7. At this time, magnesium oxide and/or sodium hydroxide are preferably as a taste masking agent. Glycerin and/or sorbitol may be used as the plasticizer. A solvent may be used to prepare the composition. The solvent may be selected from the group consisting of, but not limited to, propylene glycol, Polyoxyl 35 castor oil, Polyethylene glycol 400, Polyethylene glycol 300, trichloromonofluoromethane, sodium hydrogen carbonate, ethyl acetate, water for injection, purified soybean oil, purified water, isopropanol, liquid paraffin, sodium chloride, ethanol, acetone, physiological saline for injection, benzyl alcohol, isopropyl myristate, anhydrous ethanol, sterile purified water, N-methylpyrrolidone, glycerin, methylene chloride, toluene, and mixtures thereof. Preferably, the solvent is be selected from the group consisting of, but not limited to, sterile purified water, water for injection, purified water, isopropanol, ethanol, methylene chloride, toluene, and mixtures thereof. More preferably, the solvent may be selected from the group consisting of, but not limited to, sterile purified water, purified water, methylene chloride, toluene, and mixtures thereof. For pH measurement, the composition is dissolved in the solvent.

Shaping: the composition is fed into a molding machine and is shaped into a film in the form of a roll. At this time, the temperature of the molding machine is adjusted to 15 to 150° C., preferably 25 to 120° C., more preferably 40 to 100° C.

Aging: The film is aged at 30 to 90% relative humidity for about 1 to about 30 days so as to have a water content suitable for slitting or cutting. The water content is preferably 15% or less.

Cutting: The aged roll is slit into smaller rolls, which are then cut to desired sizes and filled in small containers or aluminum packaging foils.

Packaging: The filled small containers or aluminum packaging foils are further packaged in small boxes or are subjected to blistering to manufacture final products.

The oral film formulation thus produced contains sildenafil or a pharmaceutically acceptable salt thereof as the active ingredient, 1.0 to 12.0% by weight of magnesium oxide (MgO) and/or sodium hydroxide (NaOH) as the taste masking agent with respect to the weight of the film, and 1.0 to 4.0% of a mixture of aspartame and Talin MD90 as the sweetening agent. The pH of the composition is maintained at 4.8 to 7. According to the method of the present invention, the film is effectively produced. The oral film formulation can be dissolved in the oral cavity and is edible without water while effectively masking the unpleasant taste of the drug. The oral film formulation has increased medication compliance of a patient and improved physical properties. In addition, the oral film formulation is rapidly disintegrated and dissolved by saliva in the oral cavity without water, so that it can be easily administrated to a patient who has difficulty in swallowing tablets.

The present invention will be explained in more detail with reference to the following examples. However, these examples are provided for illustrative purposes only and are not intended to limit the scope of the invention.

The following examples are divided into two groups: A group regarding bitter taste masking and film-forming ability (Group A) and a group regarding bitter taste masking, film-forming ability, and high dose loading (Group B), which are explained separately.

Group A

Comparative Examples 1-21

Pharmaceutical compositions for oral film preparations were prepared as shown in Tables 1 and 2. The pH values, bitter taste scores, and film-forming abilities of the compositions were evaluated based on the following criteria.

Bitter taste score: After 10 men and women aged 25-40 years were allowed to feel the tastes of the compositions, the tastes were scored based on the following criteria and the scores were averaged (the values were rounded off to two decimal places).
0: No bitter taste was felt
1: Tasteless
2: Bitter taste was perceptible
3: Slightly bitter taste was felt
4: Bitter taste was felt
5: Strong bitter taste was felt
* Film-forming ability
○: Film was readily formed
Δ: Film was formed but its marketability was poor
x: Film was not formed When film formation was judged to be impossible or film marketability was judged to be poor, the following considerations were taken into account:
Composition preparation step: Mixing uniformity, precipitation, sedimentation, phase separation, state and shape (discoloration, etc.), internal curing, surface curing, etc.
Drying step: Excessive drying, defective drying, phase separation, edge warpage (curling), bubble generation, spot generation, etc.
Slitting and cutting step: Stickiness (adhesion), film peeling (peeling from PET), embrittlement, breakage, edge roughness, etc.
Final product: Strong stimuli, delayed disintegration, delayed dissolution, disgusting odor or taste production, etc.

TABLE 1

| Ingredient | Control 1 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 |
|---|---|---|---|---|---|---|---|---|---|---|---|
| Sildenafil citrate | 74.36 | 74.00 | 70.70 | 66.90 | 74.00 | 70.70 | 66.90 | 74.00 | 70.70 | 66.90 | 74.00 |
| Propylene glycol | 1.48 | 1.50 | 1.40 | 1.30 | 1.50 | 1.40 | 1.30 | 1.50 | 1.40 | 1.30 | 1.50 |
| Polysorbate | 2.97 | 3.00 | 2.80 | 2.70 | 3.00 | 2.80 | 2.70 | 3.00 | 2.80 | 2.70 | 3.00 |
| Chocolate flavor | 1.06 | 1.10 | 1.00 | 1.00 | 1.10 | 1.00 | 1.00 | 1.10 | 1.00 | 1.00 | 1.10 |
| Pullulan | 20.13 | 20.10 | 19.10 | 18.10 | 20.10 | 19.10 | 18.10 | 20.10 | 19.10 | 18.10 | 20.10 |
| Acesulfame K | 0.00 | 0.30 | 5.00 | 10.00 | 0.00 | 0.00 | 0.00 | 0.00 | 0.00 | 0.00 | 0.00 |
| Sucralose | 0.00 | 0.00 | 0.00 | 0.00 | 0.30 | 5.00 | 10.00 | 0.00 | 0.00 | 0.00 | 0.00 |
| Aspartame | 0.00 | 0.00 | 0.00 | 0.00 | 0.00 | 0.00 | 0.00 | 0.30 | 5.00 | 10.00 | 0.00 |
| Neohesperidine DC | 0.00 | 0.00 | 0.00 | 0.00 | 0.00 | 0.00 | 0.00 | 0.00 | 0.00 | 0.00 | 0.30 |
| Talin MD90 | 0.00 | 0.00 | 0.00 | 0.00 | 0.00 | 0.00 | 0.00 | 0.00 | 0.00 | 0.00 | 0.00 |
| Licorice extract | 0.00 | 0.00 | 0.00 | 0.00 | 0.00 | 0.00 | 0.00 | 0.00 | 0.00 | 0.00 | 0.00 |
| Stevioside | 0.00 | 0.00 | 0.00 | 0.00 | 0.00 | 0.00 | 0.00 | 0.00 | 0.00 | 0.00 | 0.00 |
| Total solids content | 100 | 100 | 100 | 100 | 100 | 100 | 100 | 100 | 100 | 100 | 100 |
| Proportion of solvent used[1] | | | | | | 1.0-1.2 | | | | | |
| pH of composition | 3.89 | 4.04 | 4.01 | 4.00 | 4.03 | 4.02 | 4.08 | 4.01 | 4.06 | 4.09 | 4.06 |
| Bitter taste score | 5.0 | 5.0 | 4.8 | 4.6 | 5.0 | 4.9 | 4.8 | 5.0 | 4.5 | 4.2 | 5.0 |

[1]Proportion of solvent used: Amount of solvent relative to the total solids content (times).

TABLE 2

| Ingredient | Control 11 | Comp. Ex. 11 | Comp. Ex. 12 | Comp. Ex. 13 | Comp. Ex. 14 | Comp. Ex. 15 | Comp. Ex. 16 | Comp. Ex. 17 | Comp. Ex. 18 | Comp. Ex. 19 | Comp. Ex. 20 | Comp. Ex. 21 |
|---|---|---|---|---|---|---|---|---|---|---|---|---|
| Sildenafil citrate | 74.36 | 70.70 | 66.90 | 74.00 | 70.70 | 66.90 | 74.00 | 70.70 | 66.90 | 74.00 | 70.70 | 66.90 |
| Propylene glycol | 1.48 | 1.40 | 1.30 | 1.50 | 1.40 | 1.30 | 1.50 | 1.40 | 1.30 | 1.50 | 1.40 | 1.30 |
| Polysorbate 20 | 2.97 | 2.80 | 2.70 | 3.00 | 2.80 | 2.70 | 3.00 | 2.80 | 2.70 | 3.00 | 2.80 | 2.70 |
| Chocolate flavor | 1.06 | 1.00 | 1.00 | 1.10 | 1.00 | 1.00 | 1.10 | 1.00 | 1.00 | 1.10 | 1.00 | 1.00 |
| Pullulan | 20.13 | 19.10 | 18.10 | 20.10 | 19.10 | 18.10 | 20.10 | 19.10 | 18.10 | 20.10 | 19.10 | 18.10 |
| Acesulfame K | 0.00 | 0.00 | 0.00 | 0.00 | 0.00 | 0.00 | 0.00 | 0.00 | 0.00 | 0.00 | 0.00 | 0.00 |
| Sucralose | 0.00 | 0.00 | 0.00 | 0.00 | 0.30 | 0.00 | 0.00 | 0.00 | 0.00 | 0.00 | 0.00 | 0.00 |
| Aspartame | 0.00 | 0.00 | 0.00 | 0.00 | 0.00 | 0.00 | 0.00 | 0.00 | 0.00 | 0.00 | 0.00 | 0.00 |
| Neohesperidine DC | 0.00 | 5.00 | 10.00 | 0.00 | 0.00 | 0.00 | 0.00 | 0.00 | 0.00 | 0.00 | 0.00 | 0.00 |
| Talin MD90 | 0.00 | 0.00 | 0.00 | 0.30 | 5.00 | 10.00 | 0.00 | 0.00 | 0.00 | 0.00 | 0.00 | 0.00 |
| Licorice extract | 0.00 | 0.00 | 0.00 | 0.00 | 0.00 | 0.00 | 0.30 | 5.00 | 10.00 | 0.00 | 0.00 | 0.00 |
| Stevioside | 0.00 | 0.00 | 0.00 | 0.00 | 0.00 | 0.00 | 0.00 | 0.00 | 0.00 | 0.30 | 5.00 | 10.00 |
| Total solids content | 100 | 100 | 100 | 100 | 100 | 100 | 100 | 100 | 100 | 100 | 100 | 100 |
| Proportion of solvent used[1] | | | | | | | 1.0-1.12 | | | | | | |

TABLE 2-continued

| Ingredient | Control 11 | Comp. Ex. 11 | Comp. Ex. 12 | Comp. Ex. 13 | Comp. Ex. 14 | Comp. Ex. 15 | Comp. Ex. 16 | Comp. Ex. 17 | Comp. Ex. 18 | Comp. Ex. 19 | Comp. Ex. 20 | Comp. Ex. 21 |
|---|---|---|---|---|---|---|---|---|---|---|---|---|
| pH of composition | 3.89 | 4.03 | 4.01 | 4.02 | 4.00 | 4.02 | 4.01 | 4.03 | 4.04 | 4.08 | 4.07 | 4.09 |
| Bitter taste score | 5.0 | 4.6 | 4.4 | 5.0 | 4.3 | 4.1 | 5.0 | 4.6 | 4.5 | 5.0 | 4.9 | 4.7 |

[1]Proportion of solvent used: Amount of solvent relative to the total solids content (times).

As can be seen from the results in Tables 1 and 2, the bitter taste of sildenafil citrate was not masked by the sweetening agent alone.

Examples 1-27

Pharmaceutical compositions for oral film preparations were prepared as shown in Tables 3 and 4, and their pH values, bitter taste scores, and film-forming abilities were evaluated.

TABLE 3

| Ingredient | C1 | #1 | #2 | #3 | #4 | #5 | #6 | #7 | #8 | #9 | #10 | #11 | #12 |
|---|---|---|---|---|---|---|---|---|---|---|---|---|---|
| Sildenafil citrate | 74.36 | 73.61 | 70.70 | 66.90 | 73.61 | 70.70 | 66.90 | 73.61 | 70.70 | 66.90 | 73.61 | 70.70 | 66.90 |
| Propylene glycol | 1.48 | 1.47 | 1.40 | 1.30 | 1.47 | 1.40 | 1.30 | 1.47 | 1.40 | 1.30 | 1.47 | 1.40 | 1.30 |
| Polysorbate 20 | 2.97 | 2.94 | 2.80 | 2.70 | 2.94 | 2.80 | 2.70 | 2.94 | 2.80 | 2.70 | 2.94 | 2.80 | 2.70 |
| Chocolate flavor | 1.06 | 1.05 | 1.00 | 1.00 | 1.05 | 1.00 | 1.00 | 1.05 | 1.00 | 1.00 | 1.05 | 1.00 | 1.00 |
| Pullulan | 20.13 | 19.93 | 19.10 | 18.10 | 19.93 | 19.10 | 18.10 | 19.93 | 19.10 | 18.10 | 19.93 | 19.10 | 18.10 |
| Sodium hydroxide | 0.00 | 1.00 | 5.00 | 10.00 | 0.00 | 0.00 | 0.00 | 0.00 | 0.00 | 0.00 | 0.00 | 0.00 | 0.00 |
| Calcium phosphate | 0.00 | 0.00 | 0.00 | 0.00 | 1.00 | 5.00 | 10.00 | 0.00 | 0.00 | 0.00 | 0.00 | 0.00 | 0.00 |
| Potassium hydroxide | 0.00 | 0.00 | 0.00 | 0.00 | 0.00 | 0.00 | 0.00 | 1.00 | 5.00 | 10.00 | 0.00 | 0.00 | 0.00 |
| Calcium hydroxide | 0.00 | 0.00 | 0.00 | 0.00 | 0.00 | 0.00 | 0.00 | 0.00 | 0.00 | 0.00 | 1.00 | 5.00 | 10.00 |
| Magnesium oxide | 0.00 | 0.00 | 0.00 | 0.00 | 0.00 | 0.00 | 0.00 | 0.00 | 0.00 | 0.00 | 0.00 | 0.00 | 0.00 |
| Potassium dihydrogen phosphate | 0.00 | 0.00 | 0.00 | 0.00 | 0.00 | 0.00 | 0.00 | 0.00 | 0.00 | 0.00 | 0.00 | 0.00 | 0.00 |
| Sodium dihydrogen phosphate | 0.00 | 0.00 | 0.00 | 0.00 | 0.00 | 0.00 | 0.00 | 0.00 | 0.00 | 0.00 | 0.00 | 0.00 | 0.00 |
| Calcium chloride | 0.00 | 0.00 | 0.00 | 0.00 | 0.00 | 0.00 | 0.00 | 0.00 | 0.00 | 0.00 | 0.00 | 0.00 | 0.00 |
| Potassium chloride | 0.00 | 0.00 | 0.00 | 0.00 | 0.00 | 0.00 | 0.00 | 0.00 | 0.00 | 0.00 | 0.00 | 0.00 | 0.00 |
| Total solids content (%) | 100 | 100 | 100 | 100 | 100 | 100 | 100 | 100 | 100 | 100 | 100 | 100 | 100 |
| Proportion of solvent used[1] | | | | | | | 1.0-1.2 | | | | | | |
| pH of composition | 3.89 | 4.41 | 5.24 | 5.81 | 3.97 | 4.16 | 4.23 | 4.22 | 4.41 | 4.48 | 4.17 | 4.32 | 4.51 |
| Bitter taste score | 5.0 | 3.5 | 1.9 | 1.2 | 4.7 | 4.3 | 4.1 | 4.8 | 4.4 | 2.1 | 4.9 | 4.1 | 1.9 |
| Whether or not film was formed | ○ | ○ | ○ | x | ○ | ○ | Δ | ○ | ○ | x | ○ | ○ | x |

[1]Proportion of solvent used: Amount of solvent relative to the total solids content (times).

TABLE 4

| Ingredient | C1 | #13 | #14 | #15 | #16 | #17 | #18 | #19 | #20 |
|---|---|---|---|---|---|---|---|---|---|
| Sildenafil citrate | 74.36 | 73.61 | 70.70 | 66.90 | 73.61 | 70.70 | 66.90 | 73.61 | 70.70 |

TABLE 4-continued

| Ingredient | | | | | | | | | |
|---|---|---|---|---|---|---|---|---|---|
| Propylene glycol | 1.48 | 1.47 | 1.40 | 1.30 | 1.47 | 1.40 | 1.30 | 1.47 | 1.40 |
| Polysorbate 20 | 2.97 | 2.94 | 2.80 | 2.70 | 2.94 | 2.80 | 2.70 | 2.94 | 2.80 |
| Chocolate flavor | 1.06 | 1.05 | 1.00 | 1.00 | 1.05 | 1.00 | 1.00 | 1.05 | 1.00 |
| Pullulan | 20.13 | 19.93 | 19.10 | 18.10 | 19.93 | 19.10 | 18.10 | 19.93 | 19.10 |
| Sodium hydroxide | 0.00 | 0.00 | 0.00 | 0.00 | 0.00 | 0.00 | 0.00 | 0.00 | 0.00 |
| Calcium phosphate | 0.00 | 0.00 | 0.00 | 0.00 | 0.00 | 0.00 | 0.00 | 0.00 | 0.00 |
| Potassium hydroxide | 0.00 | 0.00 | 0.00 | 0.00 | 0.00 | 0.00 | 0.00 | 0.00 | 0.00 |
| Calcium hydroxide | 0.00 | 10.00 | 0.00 | 0.00 | 0.00 | 0.00 | 0.00 | 0.00 | 0.00 |
| Magnesium oxide | 0.00 | 1.00 | 5.00 | 10.00 | 0.00 | 0.00 | 0.00 | 0.00 | 0.00 |
| Potassium dihydrogen phosphate | 0.00 | 0.00 | 0.00 | 0.00 | 1.00 | 5.00 | 10.00 | 0.00 | 0.00 |
| Sodium dihydrogen phosphate | 0.00 | 0.00 | 0.00 | 0.00 | 0.00 | 0.00 | 0.00 | 1.00 | 5.00 |
| Calcium chloride | 0.00 | 0.00 | 0.00 | 0.00 | 0.00 | 0.00 | 0.00 | 0.00 | 0.00 |
| Potassium chloride | 0.00 | 0.00 | 0.00 | 0.00 | 0.00 | 0.00 | 0.00 | 0.00 | 0.00 |
| Total solids content (%) | 100 | 100 | 100 | 100 | 100 | 100 | 100 | 100 | 100 |
| Proportion of solvent used[1] | | | | | 1.0-1.2 | | | | |
| pH of composition | 3.89 | 4.31 | 4.41 | 4.78 | 4.07 | 4.16 | 4.24 | 4.08 | 4.21 |
| Bitter taste score | 5.0 | 4.1 | 3.5 | 1.9 | 4.5 | 4.0 | 3.9 | 4.6 | 4.1 |
| Whether or not film was formed | ○ | Δ | Δ | ○ | ○ | Δ | ○ | ○ | ○ |

| Ingredient | #21 | #22 | #23 | #24 | #25 | #26 | #27 |
|---|---|---|---|---|---|---|---|
| Sildenafil citrate | 66.90 | 74.00 | 70.70 | 66.90 | 74.00 | 70.70 | 66.90 |
| Propylene glycol | 1.30 | 1.50 | 1.40 | 1.30 | 1.50 | 1.40 | 1.30 |
| Polysorbate 20 | 2.70 | 3.00 | 2.80 | 2.70 | 3.00 | 2.80 | 2.70 |
| Chocolate flavor | 1.00 | 1.10 | 1.00 | 1.00 | 1.10 | 1.00 | 1.00 |
| Pullulan | 18.10 | 20.10 | 19.10 | 18.10 | 20.10 | 19.10 | 18.10 |
| Sodium hydroxide | 0.00 | 0.00 | 0.00 | 0.00 | 0.00 | 0.00 | 0.00 |
| Calcium phosphate | 0.00 | 0.00 | 0.00 | 0.00 | 0.00 | 0.00 | 0.00 |
| Potassium hydroxide | 0.00 | 0.00 | 0.00 | 0.00 | 0.00 | 0.00 | 0.00 |
| Calcium hydroxide | 0.00 | 0.00 | 0.00 | 0.00 | 0.00 | 0.00 | 0.00 |
| Magnesium oxide | 0.00 | 0.00 | 0.00 | 0.00 | 0.00 | 0.00 | 0.00 |
| Potassium dihydrogen phosphate | 0.00 | 0.00 | 0.00 | 0.00 | 0.00 | 0.00 | 0.00 |
| Sodium dihydrogen phosphate | 10.00 | 0.00 | 0.00 | 0.00 | 0.00 | 0.00 | 0.00 |
| Calcium chloride | 0.00 | 0.30 | 5.00 | 10.00 | 0.00 | 0.00 | 0.00 |
| Potassium chloride | 0.00 | 0.00 | 0.00 | 0.00 | 0.30 | 5.00 | 10.00 |
| Total solids content (%) | 100 | 100 | 100 | 100 | 100 | 100 | 100 |
| Proportion of solvent used[1] | | | | 1.0-1.2 | | | |
| pH of composition | 4.45 | 4.01 | 4.15 | 4.19 | 4.18 | 4.31 | 4.44 |

TABLE 4-continued

| | | | | | | | |
|---|---|---|---|---|---|---|---|
| Bitter taste score | 3.4 | 4.7 | 3.8 | 3.7 | 4.6 | 3.7 | 3.7 |
| Whether or not film was formed | x | ○ | ○ | Δ | ○ | ○ | x |

[1]Proportion of solvent used: Amount of solvent relative to the total solids content (times).

As can be seen from the results in Tables 3 and 4, when the pH values of the compositions were adjusted to 4.41 or more (a maximum of pH 5.81) using the single alkalizing agent, the bitter taste was effectively masked but the film-forming abilities were greatly deteriorated. As a result, the compositions were not suitable for the production of oral film formulations.

Examples 28-40

Pharmaceutical compositions for oral film preparations were prepared as shown in Table 5, and their pH values, bitter taste scores, and film-forming abilities were evaluated.

TABLE 5

| Ingredient | Control 1 | Ex. 28 | Ex. 29 | Ex. 30 | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|---|---|---|---|
| Sildenafil citrate | 74.36 | 73.62 | 72.87 | 71.39 | 70.64 | 70.64 | 70.64 | 70.64 | 70.64 | 69.90 | 68.42 | 66.94 | 65.45 | 63.95 |
| Propylene glycol | 1.48 | 1.46 | 1.45 | 1.42 | 1.41 | 1.41 | 1.41 | 1.41 | 1.41 | 1.39 | 1.36 | 1.33 | 1.30 | 1.28 |
| Polysorbate 20 | 2.97 | 2.94 | 2.91 | 2.85 | 2.82 | 2.82 | 2.82 | 2.82 | 2.82 | 2.79 | 2.73 | 2.67 | 2.61 | 2.55 |
| Chocolate flavor | 1.06 | 1.05 | 1.04 | 1.02 | 1.01 | 1.01 | 1.01 | 1.01 | 1.01 | 1.00 | 0.97 | 0.95 | 0.93 | 0.91 |
| Pullulan | 20.13 | 19.93 | 19.73 | 19.32 | 19.12 | 19.12 | 19.12 | 19.12 | 19.12 | 18.92 | 18.52 | 18.11 | 17.71 | 17.31 |
| Sodium hydroxide | 0.00 | 0.50 | 1.00 | 2.00 | 1.00 | 2.00 | 2.50 | 3.00 | 4.00 | 3.00 | 4.00 | 5.00 | 6.00 | 7.00 |
| Magnesium oxide | 0.00 | 0.50 | 1.00 | 2.00 | 4.00 | 3.00 | 2.50 | 2.00 | 1.00 | 3.00 | 4.00 | 5.00 | 6.00 | 7.00 |
| Total solids content (%) | 100 | 100 | 100 | 100 | 100 | 100 | 100 | 100 | 100 | 100 | 100 | 100 | 100 | 100 |
| Proportion of solvent used[1] | | | | | | | 1.0-1.2 | | | | | | | |
| pH of composition | 3.89 | 3.92 | 4.38 | 4.77 | 4.49 | 4.75 | 4.82 | 4.89 | 5.21 | 4.96 | 5.25 | 5.29 | 5.41 | 5.58 |
| Bitter taste score | 5.0 | 3.9 | 2.0 | 1.4 | 1.9 | 1.2 | 1.3 | 1.4 | 1.3 | 1.2 | 1.2 | 1.1 | 1.0 | 0.8 |
| Whether or not film was formed | ○ | ○ | ○ | ○ | ○ | ○ | ○ | ○ | ○ | ○ | ○ | Δ | Δ | x |

[1]Proportion of solvent used: Amount of solvent relative to the total solids content (times).

As can be seen from the results in Table 5, when the combination of magnesium oxide and sodium hydroxide was used as an alkalizing agent, the bitter taste was effectively masked and good film-forming abilities were obtained.

Examples 41-44

Pharmaceutical compositions for oral film preparations were prepared as shown in Table 6, and their pH values, bitter taste scores, and film-forming abilities were evaluated.

TABLE 6

| Ingredient | Control 2 | Ex. 41 | Ex. 42 | Ex. 43 | Ex. 44 |
|---|---|---|---|---|---|
| Sildenafil citrate | 70.64 | 66.93 | 66.93 | 66.93 | 66.93 |
| Propylene glycol | 1.41 | 1.33 | 1.33 | 1.33 | 1.33 |
| Polysorbate 20 | 2.82 | 2.67 | 2.67 | 2.67 | 2.67 |
| Chocolate flavor | 1.01 | 0.95 | 0.95 | 0.95 | 0.95 |
| Pullulan | 19.12 | 18.12 | 18.12 | 18.12 | 18.12 |
| Sodium hydroxide | 2.00 | 2.5 | 2.5 | 2.5 | 2.5 |
| Magnesium oxide | 3.00 | 2.5 | 2.5 | 2.5 | 2.5 |
| Talin MD90 | 0 | 1.00 | 2.00 | 3.00 | 4.00 |
| Aspartame | 0 | 4.00 | 3.00 | 2.00 | 1.00 |
| Total solids content (%) | 100 | 100 | 100 | 100 | 100 |
| Proportion of solvent used[1] | | | 1.0-1.2 | | |
| pH of composition | 4.75 | 4.77 | 4.79 | 4.77 | 4.78 |
| Bitter taste score | 1.2 | 0.9 | 0.9 | 0.5 | 0.7 |
| Whether or not film was formed | ○ | ○ | ○ | ○ | ○ |

[1]Proportion of solvent used: Amount of solvent relative to the total solids content (times).

As can be seen from the results in Table 6, when the combination of magnesium oxide and sodium hydroxide as an alkalizing agent was mixed with Talin MD90 and aspartame in the predetermined ratio, the bitter taste was effectively masked, good film-forming abilities were obtained, and a very comfortable feeling upon taking were given.

2. Group B

Comparative Examples 1-15

Orally fast dissolving film preparations having the compositions shown in the following tables were produced. The pH values, bitter taste scores, and peel test results of the compositions, and the physical properties, i.e. bending test results, of the film preparations were evaluated based on the following criteria. In the tables, the contents of the ingredients in each film sheet are expressed in wt %.

Bitter taste score: After 10 men and women aged 25-40 years were allowed to feel the tastes of the compositions, the tastes were scored based on the following criteria and the scores were averaged (the values were rounded off to one decimal place).

1: Almost no bitter taste
2: Less bitter taste
3: Moderate bitter taste
4: Severe bitter taste
5: Very severe bitter taste
* Peel test The degree of peeling of each fast dissolving film from a PET support film was measured.

1: Very difficult to peel
2: Difficult to peel
3: Moderate to peel
4: Easy to peel
5: Very easy to peel

* Bending test

Each fast dissolving film was repeatedly folded in half with two fingers until the film was cut in half. The number of folds was counted. The bending test results shown in Tables 7-9 were obtained 30 min after unsealing of the films from aluminum packaging films. The test was conducted at 22° C. and 55% RH. It can be estimated that a higher number indicates better brittleness resistance.

TABLE 7

| Composition | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Sildenafil citrate | 46.7% (70 mg) | 46.7% (70 mg) | 70% (140 mg) | 70% (140 mg) | 70% (140 mg) | 70% (140 mg) |
| Pullulan | 38.3% | 34.3% | 17% | 17% | 17.6% | 17.1% |
| Glycerin | | | | | 1.4% | 1.4% |
| Propylene glycol | 1.4 | | | | | |
| Polyethylene glycol 600 | 4.5% | 3% | 3% | 1% | 2% | 0.5% |
| Xylitol | 3.5% | 2% | 2% | 1% | 1% | 0.5% |
| Sodium hydroxide | | 4% | | 4% | | 4% |
| Aspartame | 1.5% | 2% | 2% | 1.5% | 2% | 1.5% |
| Sucralose | 1.5% | 3% | 3% | 2.5% | 3% | 2.5% |
| Flavor | 2% | 2% | 0.5% | 0.5% | 0.5% | 0.5% |
| Menthol | 0.5% | 0.5% | 0.5% | 0.5% | 0.5% | 0.5% |
| Polysorbate 20 | 1.5% | 1.5% | 1% | 1% | 1% | 1% |
| Colorant | Slight amount | Slight amount | Slight amount | Slight amount | Slight amount | Slight amount |
| Total | 100% | 100% | 100% | 100% | 100% | 100% |
| Total weight (mg/sheet) | 150 | 150 | 200 | 200 | 200 | 200 |
| Whether or not film was formed | ○ | ○ | Δ | Δ | ○ | ○ |
| pH | 3.95 | 5.5 | 3.9 | 5.6 | 3.85 | 5.7 |
| Sensory test result | 5 | 2 | 5 | 4 | 5 | 4 |
| Bending test result | 4 | 3 | 1 | 1 | 2 | 2 |
| Peel test result | 3 | 3 | 2 | 1 | 2 | 1 |

Orally fast dissolving film preparations having the compositions shown in Tables 8-11 were produced. As for Examples 8-15, 20,000 sheets per batch were subjected to pilot testing. Casting, slitting and cutting suitabilities were further reviewed based on peel test, slitting test and cutting test results, respectively.

TABLE 8

| Composition | Comp. Ex. 7 | Comp. Ex. 8 | Ex. 1 | Ex. 2 | Ex. 3 |
|---|---|---|---|---|---|
| Sildenafil citrate | 64.9% (100 mg of sildenafil) | | 63.8% (100 mg of sildenafil) | 63.8% (100 mg of sildenafil) | 63.8% (100 mg of sildenafil) |
| Simethicone | | 55.8% | | | |
| Methocel E15 | 10.3% | | | | |
| Poloxamer L-44 | 5.2% | | | | |

TABLE 8-continued

| Composition | Comp. Ex. 7 | Comp. Ex. 8 | Ex. 1 | Ex. 2 | Ex. 3 |
|---|---|---|---|---|---|
| Pullulan | | | 17.0% | 17.0% | 17.0% |
| Polypro | 2.1% | | | | |
| Propylene glycol | 8.2% | | 8.2% | | |
| Glycerin | | | | | |
| Polyethylene glycol 600 | | | | 8.2% | |
| Xylitol | 7.2% | | | | 8.2% |
| Sorbitol | | | | | |
| Sodium hydroxide | | | 2.0% | 2.0% | 2.0% |
| Magnesium oxide | | | 0.7% | 0.7% | 0.7% |
| Aspartame | 1.0% | | 1.4% | 1.4% | 1.4% |
| Sucralose | | | 1.0% | 1.0% | 1.0% |
| Talin MD90 | | | 1.9% | 1.9% | 1.9% |
| Citric acid | | | 1.0% | 1.0% | 1.0% |
| Peppermint oil | 1.0% | | | | |
| Strawberry flavor | | | 1.0% | 1.0% | 1.0% |
| Menthol | | | 0.5% | 0.5% | 0.5% |
| Polysorbate 20 | | | 1.5% | 1.5% | 1.5% |
| FD&C Red No. 40 | | | 0.01% | 0.01% | 0.01% |
| Benzoic acid | 0.01% | | | | |
| Sodium EDTA | 0.01% | | | | |
| Total | 100.0% | | 100.0% | 100.0% | 100.0% |
| pH | 3.9 | | 4.38 | 4.4 | 4.37 |
| Sensory test result | 5 | | 5 | 5 | 5 |
| Bending test result | 2 | 3 | 1 | 1 | 1 |
| Peel test result | 3 | | 3 | 3 | 3 |

In the above table,

Comparative Example 7 corresponds to that described in U.S. Pat. No. 6,552,024.

The composition of Gas-X in Comparative Example 8 cannot be known but API is known to have the highest content (≥50%) among commercially available products.

1) Sensory test: 1—Almost no bitter taste, 2—Less bitter taste, 3—Slight bitter taste, 4—Severe bitter taste, 5—Very severe bitter taste.

2) Bending test: Each film was folded in half with two fingers until the film was cut, and the number of folds was counted. A higher number indicates less brittleness.

3) Peel test: After each film was dried, the degree of peeling of the film from a PET support film was measured. A higher number indicates easier peeling.

TABLE 9

| Composition | Ex. 4 | Ex. 5 | Ex. 6 | Ex. 7 |
|---|---|---|---|---|
| Sildenafil citrate | 63.8% | 69.8% | 67.2% | 63.2% |
| Simethicone | | | | |
| Methocel E15 | | | | |
| Poloxamer L-44 | | | | |
| Pullulan | 17.0% | 17.0% | 17.0% | 17.0% |
| Polyvinyl alcohol | | | | |
| Polypro | | | | |
| Propylene glycol | | | | |
| Glycerin | | | | |
| Polyethylene glycol 600 | | 0.5% | 0.5% | 0.5% |
| Xylitol | | | | |
| Sorbitol | 8.2% | | | |
| Sodium hydroxide | 2.0% | 4.0% | 8.0% | 12.0% |
| Magnesium oxide | 0.7% | 1.4% | 0.0% | 0.0% |
| Aspartame | 1.4% | 1.4% | 1.4% | 1.4% |
| Sucralose | 1.0% | 1.0% | 1.0% | 1.0% |
| Talin MD90 | 1.9% | 1.9% | 1.9% | 1.9% |
| Citric acid | 1.0% | | | |
| Peppermint oil | | | | |
| Strawberry flavor | 1.0% | 1.0% | 1.0% | 1.0% |
| Menthol | 0.5% | 0.5% | 0.5% | 0.5% |
| Polysorbate 20 | 1.5% | 1.5% | 1.5% | 1.5% |
| FD&C Red No. 40 | 0.01% | 0.01% | 0.01% | 0.01% |
| Benzoic acid | | | | |
| Sodium EDTA | | | | |
| Total | 100.0% | 100.0% | 100.0% | 100.0% |
| pH | 4.38 | 4.8 | 5.8 | 6.9 |
| Sensory test result | 4 | 2 | 2 | 1 |
| Bending test result | 2 | 2 | 1 | 1 |
| Peel test result | 3 | 3 | 1 | 1 |

In the above table,

1) Sensory test: 1—Almost no bitter taste, 2—Less bitter taste, 3—Slight bitter taste, 4—Severe bitter taste, 5—Very severe bitter taste 2) Bending test: Each film was folded in half with two fingers until the film was cut, and the number of folds was counted. A higher number indicates less brittleness.

3) Peel test: After each film was dried, the degree of peeling of the film from a PET support film was measured. A higher number indicates easier peeling.

TABLE 10

| Composition | Ex. 8 | Ex. 9 | Ex. 10 | Ex. 11 | Ex. 12 |
|---|---|---|---|---|---|
| Sildenafil citrate | 68.3% | 67.9 | 67.3% | 65.3% | 63.3% |
| Simethicone | | | | | |
| Methocel E15 | | | | | |
| Poloxamer L-44 | | | | | |
| Pullulan | 17.0% | 17.0% | 17.0% | 17.0% | 17.0% |
| Polyvinyl alcohol | | | | | |
| Polypro | | | | | |
| Propylene glycol | | | | | |
| Glycerin | 1.0% | 1.4% | 2.0% | 4.0% | 6.0% |
| Polyethylene glycol 600 | 0.5% | 0.5% | 0.5% | 0.5% | 0.5% |
| Xylitol | | | | | |
| Sorbitol | 0.5% | 0.5% | 0.5% | 0.5% | 0.5% |
| Sodium hydroxide | 4.0% | 4.0% | 4.0% | 4.0% | 4.0% |
| Magnesium oxide | 1.4% | 1.4% | 1.4% | 1.4% | 1.4% |
| Aspartame | 1.4% | 1.4% | 1.4% | 1.4% | 1.4% |
| Sucralose | 1.0% | 1.0% | 1.0% | 1.0% | 1.0% |
| Talin MD90 | 1.9% | 1.9% | 1.9% | 1.9% | 1.9% |
| Peppermint oil | | | | | |
| Strawberry flavor | 1.0% | 1.0% | 1.0% | 1.0% | 1.0% |
| Menthol | 0.5% | 0.5% | 0.5% | 0.5% | 0.5% |
| Polysorbate 20 | 1.5% | 1.5% | 1.5% | 1.5% | 1.5% |
| FD&C Red No. 40 | 0.01% | 0.01% | 0.01% | 0.01% | 0.01% |
| Total | 100.0% | 100.0% | 100.0% | 100.0% | 100.0% |
| Sensory test result | 1 | 1 | 1 | 1 | 1 |
| Bending test result | 1 | 2 | 3 | 4 | 5 |
| Peel test result | 20 sec | 21 sec | 23 sec | 25 sec | 28 sec |
| Disintegration test result | 5 | 5 | 5 | 4 | 3 |
| Slitting test result | ○ | ○ | ○ | ○ | ○ |
| Cutting test result | ○ | ○ | ○ | ○ | ○ |

In the above table,

1) Sensory test: 1—Almost no bitter taste, 2—Less bitter taste, 3—Slight bitter taste, 4—Severe bitter taste, 5—Very severe bitter taste.

2) Bending test: Each film was folded in half with two fingers until the film was cut, and the number of folds was counted. A higher number indicates less brittleness.

3) Peel test: After each film was dried, the degree of peeling of the film from a PET support film was measured. A higher number indicates easier peeling.

TABLE 11

| Composition | Ex. 13 | Ex. 14 | Ex. 15 | Ex. 16 |
|---|---|---|---|---|
| Sildenafil citrate | 61.3% | 59.3% | 54.3% | 50% (using sildenafil base) |
| Simethicone | | | | |
| Methocel E15 | | | | |
| Poloxamer L-44 | | | | |
| Pullulan | 17.0% | 17.0% | 17.0% | 34% |
| Polyvinyl alcohol | | | | |
| Polypro | | | | |
| Propylene glycol | | | | |
| Glycerin | 8.0% | 10.0% | 15.0% | 4% |
| Polyethylene glycol 600 | 0.5% | 0.5% | 0.5% | 3% |
| Xylitol | | | | |
| Sorbitol | 0.5% | 0.5% | 0.5% | 3.59% |
| Sodium hydroxide | 4.0% | 4.0% | 4.0% | 0% |
| Magnesium oxide | 1.4% | 1.4% | 1.4% | 0% |
| Aspartame | 1.4% | 1.4% | 1.4% | 1.4% |
| Sucralose | 1.0% | 1.0% | 1.0% | 1% |
| Talin MD90 | 1.9% | 1.9% | 1.9% | 0% |
| Peppermint oil | | | | |
| Strawberry flavor | 1.0% | 1.0% | 1.0% | 1% |
| Menthol | 0.5% | 0.5% | 0.5% | 0.5% |
| Polysorbate 20 | 1.5% | 1.5% | 1.5% | 1.5% |
| FD&C Red No. 40 | 0.01% | 0.01% | 0.01% | 0.01% |
| Total | 100.0% | 100.0% | 100.0% | 100.0% |
| Sensory test result | 1 | 1 | 1 | 1 |
| Bending test result | 6 | 7 | 10 | 3 |
| Disintegration test result | 31 sec | 34 sec | 41 sec | 50 sec |
| Peel test result | 1 | 1 | x | 5 |
| Slitting test result | ○ | ○ | ○ | ○ |
| Cutting test result | Δ | Δ | x | ○ |

In the above table,

1) Sensory test: 1—Almost no bitter taste, 2—Less bitter taste, 3—Slight bitter taste, 4—Severe bitter taste, 5—Very severe bitter taste.

2) Bending test: Each film was folded in half with two fingers until the film was cut, and the number of folds was counted. A higher number indicates less brittleness.

3) Peel test: After each film was dried, the degree of peeling of the film from a PET support film was measured. A higher number indicates easier peeling.

Example 16

As shown in Table 9, a composition was prepared using a sildenafil base instead of sildenafil citrate. In accordance with the processes described above, the composition was shaped, slit, cut, and packaged to produce a fast dissolving film. Sensory, bending, and peel tests were conducted on the fast dissolving film. Good results comparable to those of Example 10 were obtained.

The bending test was conducted by the following procedure. First, each fast dissolving film was repeatedly folded in half with two fingers until the film was cut in half. Then, the number of folds was counted. The bending test results shown in Tables 6-9 were obtained 30 min after unsealing of the films from aluminum packaging films. The test was conducted at 22° C. and 55% RH. It can be estimated that a higher number indicates better brittleness resistance.

As can be seen from the results in Table 7, the fast dissolving film of Comparative Example 2, which corresponds to that described in Korean Patent Registration No. 10-1188594, contained 72 mg of sildenafil citrate (corresponding to 50 mg of sildenafil), had a weight of 150 mg and a size of 22 mm (width)×32 mm (length) per sheet, sufficiently masked the bitter taste of sildenafil citrate, showed excellent physical properties, and had good brittleness resistance. The fast dissolving film of Comparative Example 4, which was substantially the same as that of Comparative Example 2 except for some excipients, contained 144 mg of sildenafil citrate (corresponding to 100 mg of sildenafil), had a weight of 200 mg and a size of 25 mm (width)×32 mm (length), exhibited a bitter taste, showed poor physical properties, and was not satisfactorily formed. As the content of the active ingredient increased from 70.23 mg to 140.45 mg, the bitter taste was not sufficiently masked by sodium hydroxide alone and good film-forming ability or brittleness resistance was not obtained. These results demonstrate the necessity of a new approach. The fast dissolving film of Comparative Example 6 further including 1.4% of glycerin compared to that of Comparative Example 4 was successfully formed but exhibited a bitter taste and showed poor physical properties. The films of Comparative Examples 1, 3, and 5 correspond to Comparative Examples 2, 4, and 6, respectively, except that sodium hydroxide was removed from the compositions. As expected, the films of Comparative Examples 1, 3, and 5 exhibited a very severe bitter taste and showed poor physical properties with increasing amount of the active ingredient.

Comparative Example 7 in Table 8 corresponds to an experimental example described in U.S. Pat. No. 6,552,024 and did not appear to mask the inherent bitter taste of sildenafil citrate. The film of Comparative Example 8 corresponds to Gas-X Thin Strips®, which is a high-dose fast dissolving film preparation available from Novartis. As a result of the bending test at 55% RH and 22° C. 30 min after unsealing, the film of Comparative Example 8 withstood three repeated folds, and thereafter, it was divided into two pieces.

The films of Examples 1-4 were produced using 2 wt % of sodium hydroxide with respect to the weight of each film and various plasticizers (such as propylene glycol, Polyethylene glycol 600, xylitol, and sorbitol) without the addition of glycerin. As a result of the bending and sensory tests, the films exhibited an extreme bitter taste and showed poor bending test results.

As can be seen from Examples 5-7, when 4 wt % or more of sodium hydroxide, 1.4 wt % or more of magnesium oxide, and an appropriate amount of the high-potency sweetener were used, the bitter taste was well masked but the films showed poor peel test results due to the excess amount of sodium hydroxide. Further, satisfactory brittleness results were not obtained.

As for Examples 8-14, the bitter taste was well masked by the use of 4 wt % or more of sodium hydroxide, 1.4 wt % or more of magnesium oxide and an appropriate amount of the high-potency sweetener. The use of 1-10 wt % of glycerin and the appropriate combination of Polyethylene glycol 600 and sorbitol contributed to a marked improvement in the physical strength (particularly brittleness resistance) of the sildenafil fast dissolving films, as demonstrated from the bending test results. However, when excess glycerin was used as in Example 15, poor peel test and cutting test results were obtained. Therefore, the film is not suitable for practical use as a commercially available product.

Gas-X Thin Strip® was subjected to the bending test at 55% RH and 22° C. 30 min after unsealing. As a result, the film withstood three repeated folds, and thereafter, it was divided into two pieces. Meanwhile, when the films of Examples 10-15 were subjected to the bending test under the same conditions, it was surprisingly found that the film of Example 10 withstood three repeated folds but the films of Examples 11-14 withstood seven repeated folds. The film of Example 15 showed good bending test results but was not easy to peel from a PET support film in the cutting process for packaging. Therefore, the film of Example 15 is not suitable for practical application.

As is apparent from the foregoing, the pharmaceutical compositions of the present invention can be used to produce oral film preparations containing various active ingredients as well as sildenafil or a pharmaceutically acceptable salt thereof having a bitter taste.

What is claimed is:

1. A fast dissolving film comprising sildenafil or a pharmaceutically acceptable salt thereof, a water soluble hydrocolloid, a plasticizer, and a taste masking agent;
   wherein the sildenafil or pharmaceutically acceptable salt thereof is present in an amount of at least 100 mg or at least 50% by weight with respect to the total weight of the film,
   wherein the water soluble hydrocolloid is pullulan,
   wherein the plasticizer is a mixture of propylene glycol and polysorbate, and
   wherein the taste masking agent is a mixture of sodium hydroxide and magnesium oxide, the mixture of sodium hydroxide and magnesium oxide being present in an amount of 4 to 8% by weight with respect to the total weight of the film, wherein the magnesium oxide and sodium hydroxide are in a ratio of 1:4 to 4:1.

2. A fast dissolving film comprising sildenafil or a pharmaceutically acceptable salt thereof, a water soluble hydrocolloid, a plasticizer, and a taste masking agent;
   wherein the sildenafil or pharmaceutically acceptable salt thereof is present in an amount of at least 100 mg or at least 50% by weight with respect to the total weight of the film,
   wherein the water soluble hydrocolloid is pullulan,
   wherein the plasticizer is a mixture of propylene glycol and polysorbate, and
   wherein the taste masking agent is a mixture of sodium hydroxide and magnesium oxide, the mixture of sodium hydroxide and magnesium oxide being present in an amount of 4 to 8% by weight with respect to the total weight of the film, wherein the magnesium oxide and sodium hydroxide are in a ratio of 1:1.

* * * * *